(12) United States Patent
Marcotte et al.

(10) Patent No.: US 12,708,334 B2
(45) Date of Patent: Aug. 18, 2026

(54) X-RAY IMAGING GANTRY DAMPING SYSTEM

(71) Applicant: GE Precision Healthcare LLC, Waukesha, WI (US)

(72) Inventors: Julien Marcotte, Saint-Vrain (FR); Guoli Pan, Beijing (CN); Carlos Martínez Ferreira, Paris (FR)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 130 days.

(21) Appl. No.: 18/783,922

(22) Filed: Jul. 25, 2024

(65) Prior Publication Data

US 2026/0026762 A1 Jan. 29, 2026

(51) Int. Cl.
*A61B 6/46* (2024.01)
*A61B 6/00* (2024.01)

(52) U.S. Cl.
CPC ............ *A61B 6/447* (2013.01); *A61B 6/4441* (2013.01); *A61B 6/4464* (2013.01)

(58) Field of Classification Search
CPC ...... A61B 6/4441; A61B 6/4464; A61B 6/447
See application file for complete search history.

(56) References Cited

U.S. PATENT DOCUMENTS

2021/0145383 A1* 5/2021 Barker ................. A61B 6/4441
2022/0254021 A1 8/2022 Ida et al.

FOREIGN PATENT DOCUMENTS

CN 102451012 A * 5/2012 ........... A61B 6/4291
CN 109660038 4/2019
TW 201522953 6/2015
WO 2021246696 12/2021

OTHER PUBLICATIONS

English translation of CN102451012A (Year: 2012).*

* cited by examiner

*Primary Examiner* — Mark R Gaworecki
(74) *Attorney, Agent, or Firm* — Fletcher Yoder, P.C.

(57) ABSTRACT

An X-ray imaging includes an X-ray radiation source. The X-ray imaging system also includes an X-ray detector. The X-ray imaging system further includes a gantry structure configured to be mounted to a ceiling or a floor. The gantry structure includes a C-arm having the X-ray radiation source disposed on a first end and the X-ray detector disposed on a second end opposite the first end. The gantry structure also includes a C-arm rotation device coupled to the C-arm and configured to rotate the C-arm relative in an orbital direction relative to the C-arm rotation device. The X-ray imaging system also includes a damping system coupled to the gantry structure and disposed between the gantry structure and the ceiling or the floor, wherein the damping system is configured to dampen vibrations caused by motion of the gantry structure for an entirety of the gantry structure.

19 Claims, 7 Drawing Sheets

X-RAY IMAGING GANTRY DAMPING SYSTEM

BACKGROUND

The subject matter disclosed herein relates to X-ray imaging systems and, more particularly, to a damping system (e.g., anti-vibration damping system) for an X-ray imaging system having a C-arm.

Medical diagnostic imaging systems generate images of an object, such as a patient, for example, through exposure to an energy source, such as X-rays passing through a patient, for example. The generated images may be used for many purposes. Often, when a practitioner takes X-rays of a patient, it is desirable to take several X-rays of one or more portions of the patient's body from a number of different positions and angles, and preferably without needing to frequently reposition the patient. To meet this need, C-arm X-ray diagnostic equipment has been developed. The term C-arm generally refers to an X-ray imaging device having a rigid and/or articulating structural member having an X-ray source and an image detector assembly that are each located at an opposing end of the structural member so that the X-ray source and the image detector face each other. The structural member is typically "C" shaped and so is referred to as a C-arm. In this manner, X-rays emitted from the X-ray source can impinge on the image detector and provide an X-ray image of the object or objects that are placed between the X-ray source and the image detector. During the deceleration phase of the C-arc motion of the C-arm, a lot of vibrations are generated for several seconds that may impact image quality (e.g., causing blurriness).

SUMMARY

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In accordance with an embodiment, a X-ray imaging system is provided. The X-ray imaging system includes an X-ray radiation source. The X-ray imaging system also includes an X-ray detector. The X-ray imaging system further includes a gantry structure configured to be mounted to a ceiling or a floor. The gantry structure includes a C-arm having the X-ray radiation source disposed on a first end and the X-ray detector disposed on a second end opposite the first end. The gantry structure also includes a C-arm rotation device coupled to the C-arm and configured to rotate the C-arm relative in an orbital direction relative to the C-arm rotation device. The X-ray imaging system also includes a damping system coupled to the gantry structure and disposed between the gantry structure and the ceiling or the floor, wherein the damping system is configured to dampen vibrations caused by motion of the gantry structure for an entirety of the gantry structure.

In accordance with another embodiment, a damping system for an X-ray imaging system is provided. The damping system includes a damping mechanism. The damping mechanism includes a body configured to couple to a gantry structure of the X-ray imaging system. The X-ray imaging system includes the gantry structure, an X-ray radiation source, and an X-ray detector, and the gantry structure is configured to be mounted to a ceiling or a floor. The gantry structure includes a C-arm having the X-ray radiation source disposed on a first end and the X-ray detector disposed on a second end opposite the first end, and a C-arm rotation device coupled to the C-arm and configured to rotate the C-arm in an orbital direction relative to the C-arm rotation device. The body has a third end and a fourth opposite the third end. A damping mechanism also includes a first damper connection disposed on the third end. The damping mechanism further includes a second damper connection coupled to the fourth end. The damping system also includes a swivel bearing configured to enable the gantry structure to rotate 360 degrees about a rotational axis of the swivel bearing, wherein the damping system is configured to dampen vibrations caused by motion of the gantry structure for an entirety of the gantry structure.

In accordance with a further embodiment, a, X-ray imaging system is provided. The X-ray imaging system includes an X-ray radiation source. The X-ray imaging system also includes an X-ray detector. The X-ray imaging system further includes a gantry structure configured to be mounted to a ceiling. The gantry structure includes a C-arm having the X-ray radiation source disposed on a first end and the X-ray detector disposed on a second end opposite the first end. The C-arm is made of carbon fiber. The gantry structure also includes a C-arm rotation device coupled to the C-arm and configured to rotate the C-arm relative in an orbital direction relative to the C-arm rotation device. The X-ray imaging system includes a damping system coupled to the gantry structure and disposed between the gantry structure and the ceiling. The damping system is configured to dampen vibrations caused by motion of the gantry structure for an entirety of the gantry structure along orthogonal directions. The orthogonal directions include a vertical direction extending between a floor and the ceiling and a horizontal direction that is both perpendicular to the vertical direction and parallel with the floor.

BRIEF DESCRIPTION OF THE DRAWINGS

These and other features, aspects, and advantages of the present disclosed subject matter will become better understood when the following detailed description is read with reference to the accompanying drawings in which like characters represent like parts throughout the drawings, wherein.

DETAILED DESCRIPTION

Figure 1:
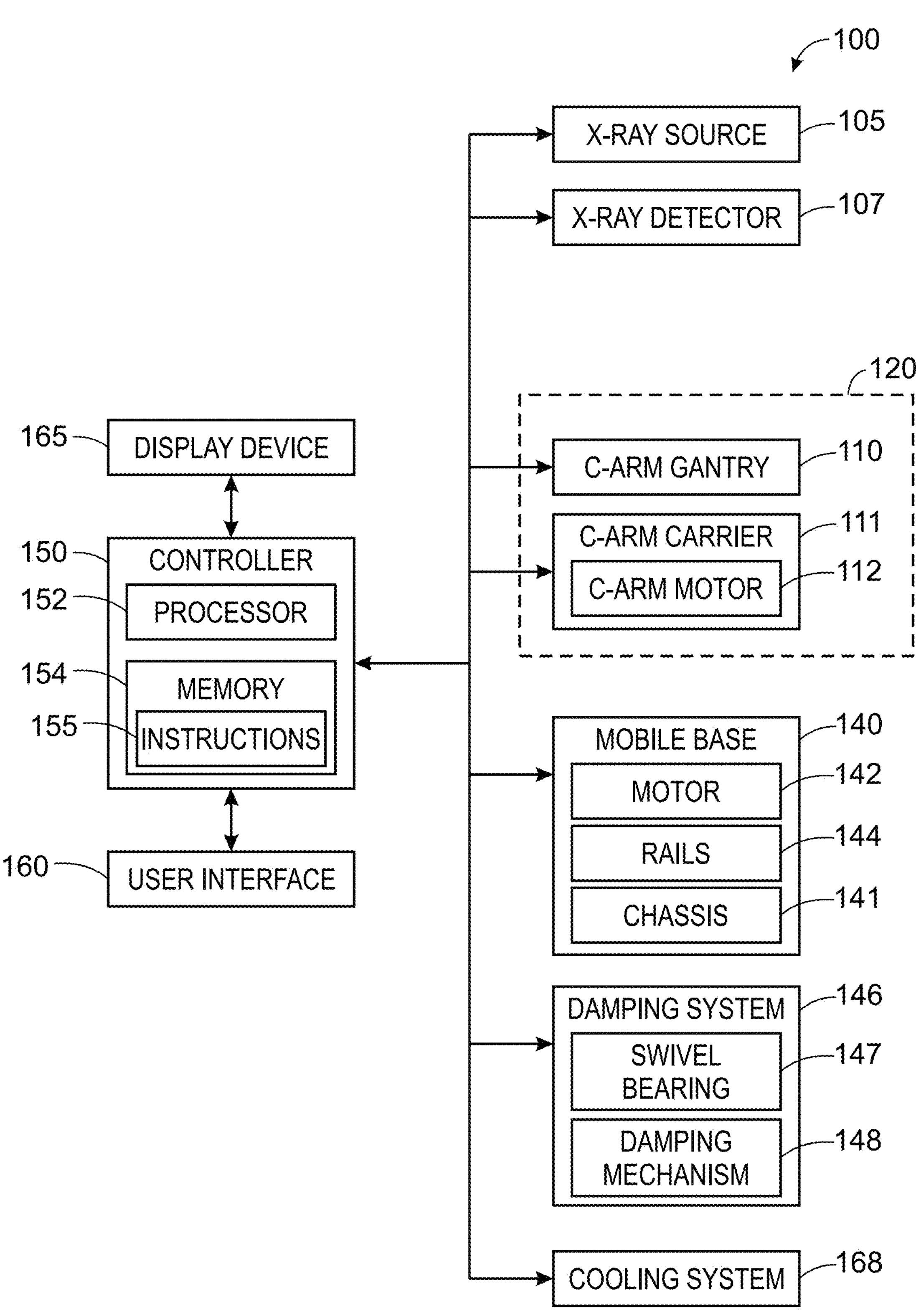
FIG. 1 is a block diagram illustrating components of an example X-ray imaging system, in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The following embodiments describe a damping system for an X-ray imaging system mounted to a floor or a ceiling in a room. The damping system dampens motion cause by floor or ceiling gantry motion in multiple axes or directions. The damping system also enables the use of a structure (e.g., as part of the gantry structure such as the C-arm) with a low damping coefficient (e.g., relative to aluminum) due to its nature or size. The damping system further enables the gantry structure (e.g., C-arm) to move with a higher speed (e.g., up to 100 degrees per second speed capacity) to make three-dimensional (3D) reconstruction faster but without causing a regression in image quality. The damping system reduces workflow time. The damping system also improves patient comfort. The damping system is also safe (i.e., allowing the X-ray imaging system to be stable) even if the damping system ceases to work.

The embodiments include an X-ray imaging including an X-ray radiation source. The X-ray imaging system also includes an X-ray detector. The X-ray imaging system further includes a gantry structure configured to be mounted to a ceiling or a floor. The gantry structure includes a C-arm having the X-ray radiation source disposed on a first end and the X-ray detector disposed on a second end opposite the first end. The gantry structure also includes a C-arm rotation device coupled to the C-arm and configured to rotate the C-arm relative in an orbital direction relative to the C-arm rotation device. The X-ray imaging system also includes a damping system coupled to the gantry structure and disposed between the gantry structure and the ceiling or the floor, wherein the damping system is configured to dampen vibrations caused by motion of the gantry structure for an entirety of the gantry structure.

In certain embodiments, the damping system includes a swivel bearing and a damping mechanism. In certain embodiments, the damping mechanism includes a body having a third end and a fourth end opposite the third end, a first damper connection disposed on the third end, and a second damper connection coupled to the fourth end. In certain embodiments, both the first damper connection and the second damper connection both directly contact both the gantry structure and the body. In certain embodiments, the first damper connection includes one or more damping pads (e.g., made of elastomeric material such as rubber). In certain embodiments, the second damper connection includes a shaft and bushings coupled to opposite ends of the shaft, and wherein the shaft extends through a portion of the gantry structure.

In certain embodiments, the swivel bearing is disposed on a surface of the body facing the floor when the gantry structure is mounted to the floor. In certain embodiments, the swivel bearing is disposed on a surface of the body facing the ceiling when the gantry structure is mounted to the ceiling. In certain embodiments, the body is made of a material that is at least times stiffer than both the first damper connection and the second damper connection. In certain embodiments, the swivel bearing is configured to enable the gantry structure to rotate 360 degrees about a rotational axis of the swivel bearing.

In certain embodiments, the damping system is configured to dampen the vibrations for the entirety of the gantry structure along multiple directions (or axes). In certain embodiments, the multiple directions include orthogonal directions, and wherein the orthogonal directions include a vertical direction extending between the floor and the ceiling and a horizontal direction that is both perpendicular to the vertical direction and parallel with the floor. In certain embodiments, wherein the C-arm is made of carbon fiber.

The embodiments also include a damping system for an X-ray imaging system is provided. The damping system includes a damping mechanism. The damping mechanism includes a body configured to couple to a gantry structure of the X-ray imaging system. The X-ray imaging system includes the gantry structure, an X-ray radiation source, and an X-ray detector, and the gantry structure is configured to be mounted to a ceiling or a floor. The gantry structure includes a C-arm having the X-ray radiation source disposed on a first end and the X-ray detector disposed on a second end opposite the first end, and a C-arm rotation device coupled to the C-arm and configured to rotate the C-arm in an orbital direction relative to the C-arm rotation device. The body has a third end and a fourth opposite the third end. A damping mechanism also includes a first damper connection disposed on the third end. The damping mechanism further includes a second damper connection coupled to the fourth end. The damping system also includes a swivel bearing configured to enable the gantry structure to rotate 360 degrees about a rotational axis of the swivel bearing, wherein the damping system is configured to dampen vibrations caused by motion of the gantry structure for an entirety of the gantry structure.

In certain embodiments, the damping system includes both the first damper connection and the second damper connection both directly contacting both the gantry structure and the body, and the first damper connection includes one or more damping pads, and the second damper connection includes a shaft and bushings coupled to opposite ends of the shaft, and the shaft extends through a portion of the gantry structure. In certain embodiments, the swivel bearing is disposed on a surface of the body facing the floor when the gantry structure is mounted to the floor. In certain embodiments, the swivel bearing is disposed on a surface of the body facing the ceiling when the gantry structure is mounted to the ceiling. In certain embodiments, the body is made of a material that is at least times stiffer than both the first damper connection and the second damper connection. In certain embodiments, the damping system is configured to dampen the vibrations for the entire gantry structure along orthogonal directions, and wherein the orthogonal directions include a vertical direction extending between the floor and the ceiling and a horizontal direction that is both perpendicular to the vertical direction and parallel with the floor.

The embodiments further include an X-ray imaging system that includes an X-ray radiation source. The X-ray imaging system also includes an X-ray detector. The X-ray imaging system further includes a gantry structure configured to be mounted to a ceiling. The gantry structure includes a C-arm having the X-ray radiation source disposed on a first end and the X-ray detector disposed on a second end opposite the first end. The C-arm is made of carbon fiber. The gantry structure also includes a C-arm rotation device coupled to the C-arm and configured to rotate the C-arm relative in an orbital direction relative to the C-arm rotation device. The X-ray imaging system includes a damping system coupled to the gantry structure and disposed between the gantry structure and the ceiling. The damping system is configured to dampen vibrations caused by motion of the gantry structure for an entirety of the gantry structure along orthogonal directions. The orthogonal directions include a vertical direction extending between a floor and the ceiling and a horizontal direction that is both perpendicular to the vertical direction and parallel with the floor.

FIG. 1 is a block diagram illustrating components of an example X-ray imaging system 100. In certain embodiments, the X-ray imaging system 100 is configured to perform vascular imaging. The X-ray imaging system 100 is configured to be mounted to a floor or a ceiling. In certain embodiments, the X-ray imaging system 100 is mounted to the floor or the ceiling at location. In certain embodiments, the X-ray imaging system 100 is mounted to the floor or the ceiling but may move along the floor or the ceiling (e.g., via chassis that moves along a rail system). The X-ray imaging system 100 includes an X-ray source 105 (or X-ray radiation source) and an X-ray detector 107 mounted on a C-arm gantry 110 (e.g., C-arm). In certain embodiments, the C-arm gantry 110 may be made of carbon fiber.

The C-arm gantry 110 is part of a gantry structure 120. The gantry structure 120 includes a C-arm motor 112 for adjusting the position of the C-arm gantry 110. More specifically, the C-arm gantry 110 is mechanically coupled to a C-arm carrier 111 (e.g., C-arm rotation device) which includes the C-arm motor 112, and the C-arm motor 112 may be driven to adjust the position of the C-arm gantry 110 with respect to the C-arm carrier 111. For example, the C-arm carrier 111 in conjunction with the C-arm motor 112 is configured to rotate the C-arm gantry 110 in an orbital direction relative to the C-arm carrier 111. In certain embodiments, the C-arm carrier 111 (via a motorized system) is configured to rotate a pivot (e.g., pivot point) where the C-arm carrier 111 is coupled to an end of an arm (e.g., L-arm) coupled or mounted to floor or to the ceiling. The C-arm carrier 111 rotates about a rotational axis (e.g., horizontal axis) of the pivot. In certain embodiments having an L-arm, the L-arm may rotate about a location where the other end of the L-arm (i.e., the end of the L-arm not connected to the pivot) is coupled to or mounted to the floor or to the ceiling (via a damping system 146). In certain embodiments, the C-arm carrier 111 is coupled to or mounted to the floor or to the ceiling (via the damping system 146).

In certain embodiments, the X-ray imaging system 100 also includes a mobile base 140. The mobile base 140 is coupled to a floor or a ceiling. In certain embodiments, the C-arm carrier 111 is coupled to the mobile base 140 via an L-arm (e.g., via the end of the L-arm not connected to the pivot) coupled to the damping system 146. In certain embodiments, the C-arm carrier 111 is coupled to the mobile base 140 via the damping system 146. The mobile base 140 is configured to move (e.g., translocate) the X-ray imaging system 100 from one location to another location (e.g., in a linear direction) on the floor or the ceiling. The mobile base 140 includes a chassis 141. The mobile base 140 also includes a motor 142 and a rail system 144 (e.g., having rails). The rail system 144 is directly coupled to the floor or the ceiling. The motor 142 is configured to drive movement of the chassis 141 and, thus, the X-ray imaging system 100 along the rail system 144 (e.g., to adjust a position of the X-ray imaging system 100).

The X-ray imaging system 100 further includes a damping system 146. The damping system 146 is configured to dampen vibrations that occur when the C-arm gantry 110 (e.g., made of carbon fiber) moves and/or deaccelerates (e.g., during the deacceleration phase) to a stop during movement of the gantry structure 120 along multiple axes or directions (e.g., combined directions). For example, the movement of the gantry structure 120 may include the rotational movement of the C-arm gantry 110 in the orbital direction, rotational movement about the axis of the pivot where the C-arm carrier 111 is coupled to an end of an arm (e.g., L-arm), and/or rotation about where an axis of where the damping system 146 (e.g., axis of the swivel bearing 147) is coupled to the floor or the ceiling. The damping system 146 is configured to dampen vibrations caused by movement of the gantry structure 120 for an entirety of the gantry structure 120 along the multiple directions. The multiple directions may include orthogonal directions. For example, the orthogonal directions may include a vertical direction extending between a floor and the ceiling and a horizontal direction that is both perpendicular to the vertical direction and parallel with the floor.

The damping system 146 includes a swivel bearing 147 and a damping mechanism 148. The damping mechanism 148 includes a body having a first end and a second end opposite the first end, a first damper connection disposed on the first end, and a second damper connection coupled to the second end. In certain embodiments, both the first damper connection and the second damper connection both directly contact both the gantry structure 120 and the body. In certain embodiments, the first damper connection includes one or more damping pads or dampers (e.g., made of elastomeric material such as rubber). In certain embodiments, the second damper connection includes a shaft and bushings coupled to opposite ends of the shaft, and wherein the shaft extends through a portion of the gantry structure 120.

In certain embodiments, the swivel bearing 147 is disposed on a surface of the body facing the floor when the gantry structure 120 is mounted to the floor. In certain embodiments, the swivel bearing 147 couples the gantry structure 120 to the mobile base 140 (e.g., the chassis) when the X-ray imaging system 100 is mounted to the ceiling. In certain embodiments, the swivel bearing 147 is disposed on a surface of the body facing the ceiling when the gantry structure 120 is mounted to the ceiling. In certain embodiments, the swivel bearing 147 couples the gantry structure 120 to the mobile base 140 (e.g., the chassis) when the X-ray imaging system 100 is mounted to the floor. In certain embodiments, the swivel bearing 147 couples the gantry structure 120 directly to the floor (i.e., where there is no mobile base 140) when the X-ray imaging system 100 is mounted to the floor. In certain embodiments, the body is made of a material that is at least times stiffer than both the first damper connection and the second damper connection. The swivel bearing 147 is configured to enable the gantry structure 120 to rotate 360 degrees about a rotational axis of the swivel bearing 147.

The X-ray imaging system 100 further includes a controller 150 including a processor 152 and a non-transitory memory 154. A method for controlling the X-ray imaging system 100 may be stored as executable instructions 155 in the non-transitory memory 154 and executed by the processor 152.

The X-ray imaging system 100 further include a user interface 160 for receiving input from a user or operator of the X-ray imaging system 100. The user interface 160 may be communicatively coupled to the controller 150 for providing commands input by a user via the user interface 160 to the controller 150. The user interface 160 may include one or more of a keyboard, a mouse, a trackball, one or more knobs, one or more joysticks, a touchpad, a touchscreen, one or more hard and/or soft buttons, a smartphone, a microphone, a virtual reality apparatus, and so on. The user interface 160 may thus enable voice control, and display of information such as an interactive display device (e.g., touchscreen). In some examples the user interface 160 may be remotely located relative to the X-ray imaging system 100. For example, the user interface 160 may be communicatively coupled to the controller 150 and/or the X-ray imaging system 100 via a wired or wireless connection, and may be positioned away from the mobile base 140.

As an example, the memory 154 may store processor-executable software code or instructions (e.g., firmware or software), which are tangibly stored on a non-transitory computer readable medium. Additionally or alternatively, the memory 154 may store data. As an example, the memory 154 may include a volatile memory, such as random access memory (RAM), and/or a nonvolatile memory, such as read-only memory (ROM), flash memory, a hard drive, or any other suitable optical, magnetic, or solid-state storage medium, or a combination thereof. Furthermore, the processor 152 may include multiple microprocessors, one or more "general-purpose" microprocessors, one or more special-purpose microprocessors, and/or one or more application specific integrated circuits (ASICS), or some combination thereof. For example, the processor 152 may include one or more reduced instruction set (RISC) or complex instruction set (CISC) processors. The processor 152 may include multiple processors, and/or the memory 154 may include multiple memory devices.

A user of the X-ray imaging system 100 may input a desired isocenter position via the user interface 160, for example. The controller 150 may then determine position adjustments to one or more of the C-arm gantry 110 and/or the mobile base 140 to align an isocenter of the X-ray imaging system 100 with the desired isocenter position. As another example, a user of the X-ray imaging system 100 may directly control the position of one or more components of the X-ray imaging system 100 relative to other components of the X-ray imaging system 100 via the user interface 160. For example, the user may directly input, via a joystick or knob, for example, position adjustments to one or more components of the X-ray imaging system 100. As another example, the motion of the components of the X-ray imaging system 100 may be pre-programmed such that the user does not directly control any movement, but instead initiates the start of the pre-programmed motion. The motion may include complex motions, with continuous motion of the isocenter.

The controller 150 is further communicatively coupled to a display device 165 for displaying one or more X-ray images acquired via the X-ray detector 107. Further, in some examples, one or more of the controller 150, the user interface 160, and the display device 165 may be positioned away from (e.g., remotely from) the remaining components of the X-ray imaging system 100.

The X-ray imaging system 100 may further include a cooling system 168 for cooling the X-ray source 105 and/or the X-ray detector 107. The cooling system 168 may include one or more flexible tubes and a pump, as an illustrative and non-limiting example, for providing cooling fluid to the X-ray source 105 to transfer thermal energy away from the X-ray source 105. The cooling system 168 may actively cool the X-ray source 105 and the X-ray detector 107 independently, or in some examples may cool the X-ray detector 107 by any suitable type of derivation of the cooling circuit for the X-ray source 105.

Figure 2:
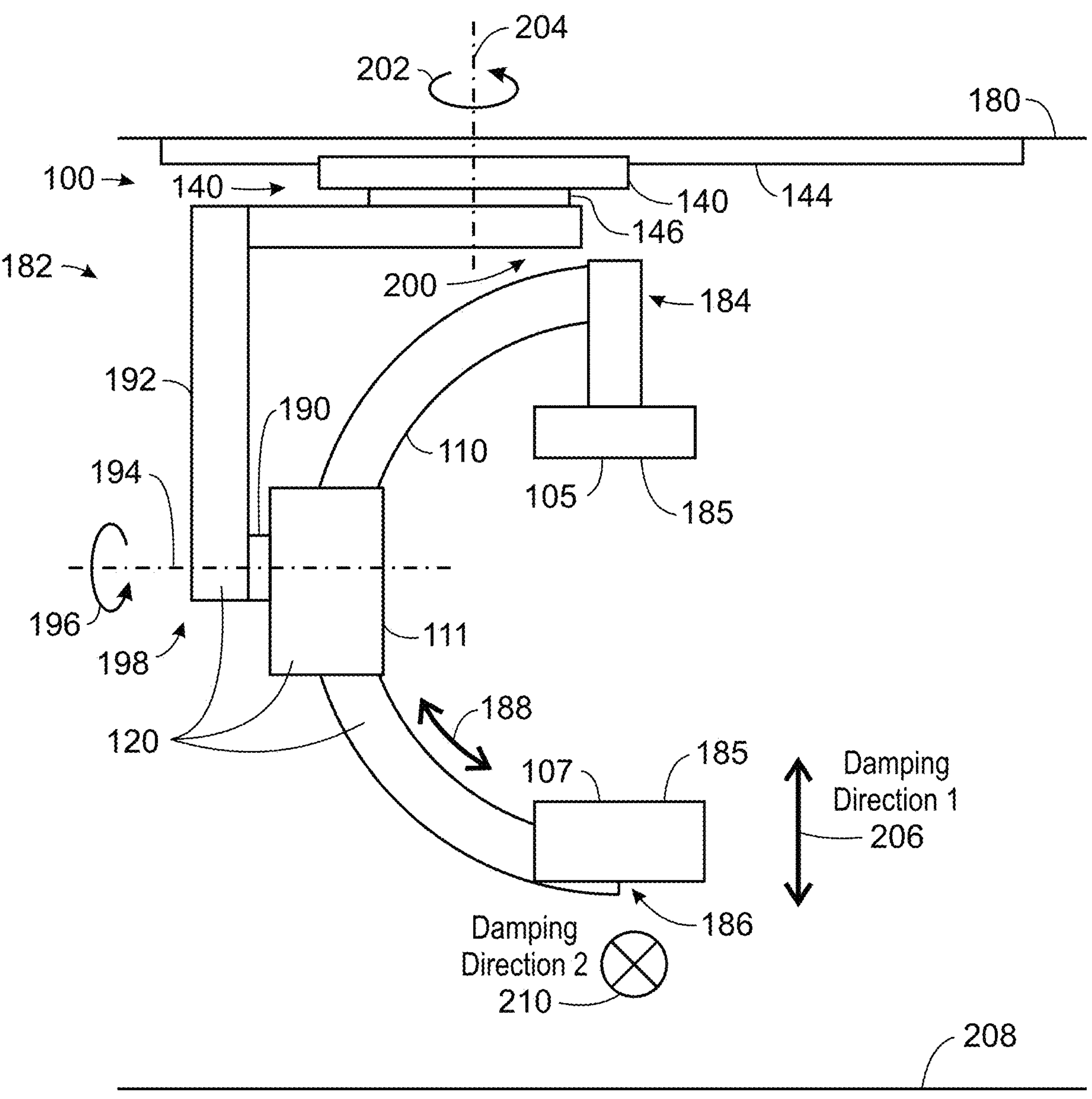
FIG. 2 is a schematic diagram of a side view of an X-ray imaging system (e.g., having an L-arm) mounted to a ceiling, in accordance with aspects of the present disclosure.

FIG. 2 is a schematic diagram of a side view of the X-ray imaging system 100 (e.g., having an L-arm) mounted to a ceiling 180 (e.g., in a room 182). The X-ray imaging system 100 includes the C-arm gantry 110. In certain embodiments, the C-arm gantry 110 is made of carbon fiber. The X-ray imaging system 100 also includes the X-ray radiation source 105 coupled to a first end 184 of the C-arm gantry 110 and the X-ray detector 107 coupled to a second end 186 of the C-arm gantry 110 opposite the first end 184 (e.g., forming the image chain 185).

The C-arm gantry 110 is coupled to the C-arm carrier 111 (e.g., C-arm rotation device) is configured to rotate the C-arm gantry 110 in an orbital direction 188 relative to the C-arm carrier 111 about an isocenter (of the X-ray radiation source 105 and the X-ray detector 107). The C-arm carrier 111 includes rollers (e.g., guiding rollers) to guide movement of the C-arm gantry 110 relative to the C-arm carrier 111.

The C-arm carrier 111 is coupled to a pivot 190 (e.g., pivot point or shaft). The pivot 190 is coupled to a structure 192. The pivot 190 (in conjunction with a motorized system) that is configured to rotate both the C-arm carrier 111 and the C-arm gantry 110 about a rotational axis 194 (e.g., horizontal axis) of the pivot 190 as indicated by arrow 196. In certain embodiments, the structure 192 is an L-arm coupled to the mobile base 140 via the damping system 146. The pivot 190 is coupled to a first end 198 of the L-arm and the damping system 146 is coupled to a second end 200 of the L-arm. The damping system 146 is configured to couple the gantry structure 120 to the mobile base 140 (and, thus, mount the X-ray imaging system 100 to the ceiling 180). In certain embodiments, the L-arm may rotate about an end of the L-arm coupled to the mobile base 140 via the swivel bearing of the damping system 146. In particular, the L-arm (and the gantry structure 120) rotate in direction 202 about a rotational axis 204 of the swivel bearing.

As mentioned, the damping system 146 is coupled to the mobile base 140. In particular, the damping system 146 is coupled to the chassis 141. The chassis 141 (driven by a motor) is configured to move the X-ray imaging system 100 along the rail system 144.

The damping system 146 is configured to dampen vibrations caused by motion of the gantry structure 120 for an entirety of the gantry structure 120. For example, the movement of the gantry structure 120 may include the rotational movement of the C-arm gantry 110 in the orbital direction 188, rotational movement in the direction 196 about the axis 194 of the pivot 190 where the C-arm carrier 111 is coupled to an end of the structure 192 (e.g., L-arm), and/or rotational movement in the direction 202 about the 204 axis of where the damping system 146 (e.g., axis 204 of the swivel bearing) is coupled to the ceiling 180. The damping system 146 is configured to dampen vibrations caused by movement of the gantry structure 120 for an entirety of the gantry structure 120 along the multiple directions. The multiple directions may include orthogonal directions. For example, the orthogonal directions may include a vertical direction 206 extending between a floor 208 and the ceiling 180 and a horizontal direction 210 (into the page in FIG. 2) that is both perpendicular to the vertical direction 206 and parallel with the floor 208.

In certain embodiments, the damping system includes a swivel bearing (e.g., which couples the gantry structure to the ceiling 180) and a damping mechanism. The damping mechanism includes a body having a first end and a second end opposite the first end, a first damper connection disposed on the first end, and a second damper connection coupled to the second end. In certain embodiments, both the first damper connection and the second damper connection both directly contact both the gantry structure 120 and the body. In certain embodiments, the first damper connection includes one or more damping pads or dampers (e.g., made of elastomeric material such as rubber). In certain embodiments, the second damper connection includes a shaft and bushings coupled to opposite ends of the shaft, and wherein the shaft extends through a portion of the gantry structure 120. In certain embodiments, the swivel bearing is disposed on a surface of the body facing the ceiling 180 when the gantry structure 120 is mounted to the ceiling 180.

Figure 3:
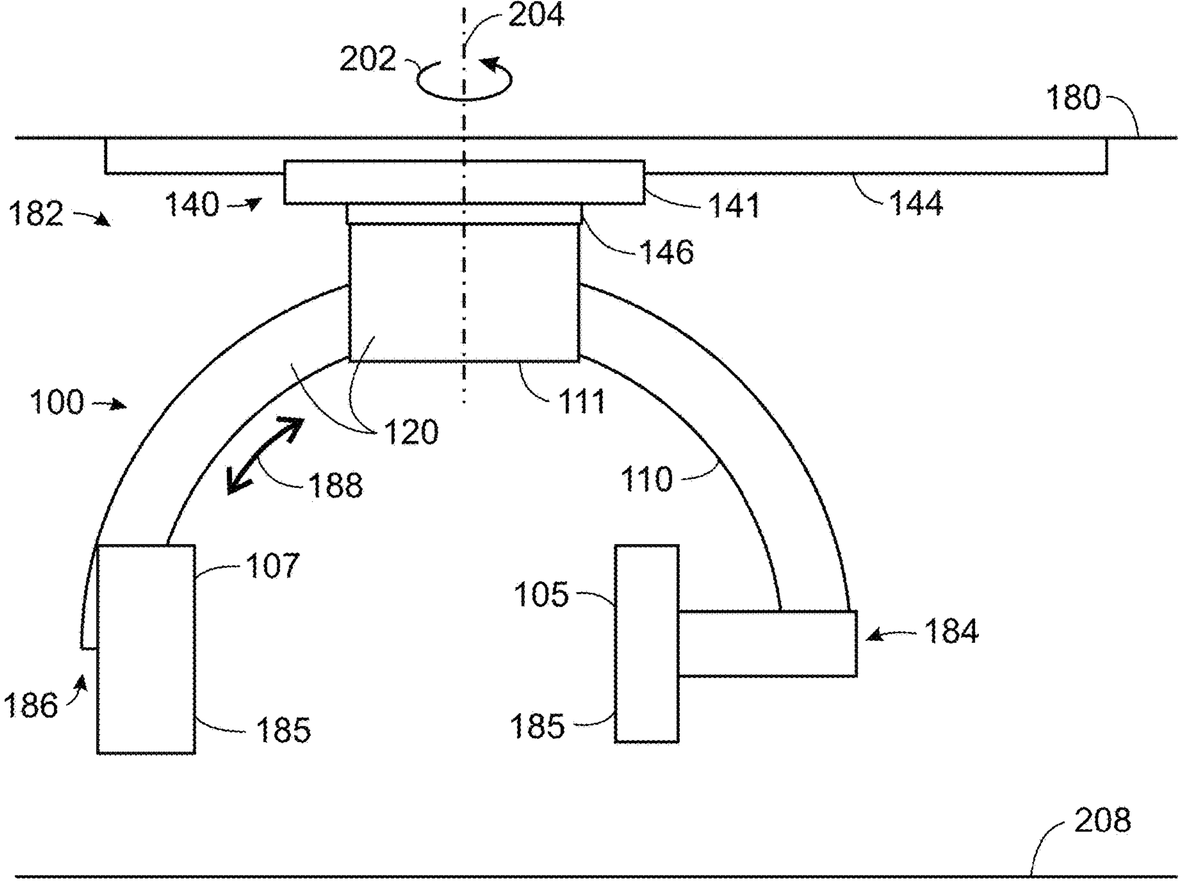
FIG. 3 is a schematic diagram of a side view of an X-ray imaging system (e.g., lacking an L-arm) mounted to a ceiling, in accordance with aspects of the present disclosure.

FIG. 3 is a schematic diagram of a side view of the X-ray imaging system 100 (e.g., lacking an L-arm) mounted to a ceiling 180 (e.g., in a room 182). The X-ray imaging system 100 includes the C-arm gantry 110. In certain embodiments, the C-arm gantry 110 is made of carbon fiber. The X-ray imaging system 100 also includes the X-ray radiation source 105 coupled to the first end 184 of the C-arm gantry 110 and the X-ray detector 107 coupled to the second end 186 of the C-arm gantry 110 opposite the first end 184 (e.g., forming the image chain 185).

The C-arm gantry 110 is coupled to the C-arm carrier 111 (e.g., C-arm rotation device) that is configured to rotate the C-arm gantry 110 in an orbital direction 188 relative to the C-arm carrier 111 about an isocenter (of the X-ray radiation source 105 and the X-ray detector 107). The C-arm carrier 111 includes rollers (e.g., guiding rollers) to guide movement of the C-arm gantry 110 relative to the C-arm carrier 111.

The C-arm carrier 111 is directly coupled to the damping system 146. The damping system 146 is coupled to the mobile base 140 and, thus, mounted to ceiling 180). The gantry structure 120 (e.g., the C-arm 110) may rotate about the C-arm carrier 111 is coupled to the mobile base 140 via the swivel bearing of the damping system 146. In particular, the C-arm carrier 111 (and the gantry structure 120 including the C-arm 110) rotate in the direction 202 about the rotational axis 204 of the swivel bearing.

As mentioned, the damping system 146 is coupled to the mobile base 140. In particular, the damping system 146 is coupled to the chassis 141. The chassis 141 (driven by a motor) is configured to move the X-ray imaging system 100 along the rail system 144.

The damping system 146 is configured to dampen vibrations caused by motion of the gantry structure 120 for an entirety of the gantry structure 120. For example, the movement of the gantry structure 120 may include the rotational movement of the C-arm gantry 110 in the orbital direction 188 and/or rotational movement in the direction 202 about the 204 axis of where the damping system 146 (e.g., axis 204 of the swivel bearing) is coupled to the ceiling 180. The damping system 146 is configured to dampen vibrations caused by movement of the gantry structure 120 for an entirety of the gantry structure 120 along the multiple directions. The multiple directions may include orthogonal directions. For example, the orthogonal directions may include a vertical direction extending between a floor 208 and the ceiling 180 and a horizontal direction that is both perpendicular to the vertical direction and parallel with the floor 208 as depicted in FIG. 2.

In certain embodiments, the damping system includes a swivel bearing (e.g., which couples the gantry structure to the ceiling 180) and a damping mechanism. The damping mechanism includes a body having a first end and a second end opposite the first end, a first damper connection disposed on the first end, and a second damper connection coupled to the second end. In certain embodiments, both the first damper connection and the second damper connection both directly contact both the gantry structure 120 and the body. In certain embodiments, the first damper connection includes one or more damping pads or dampers (e.g., made of elastomeric material such as rubber). In certain embodiments, the second damper connection includes a shaft and bushings coupled to opposite ends of the shaft, and wherein the shaft extends through a portion of the gantry structure 120. In certain embodiments, the swivel bearing is disposed on a surface of the body facing the ceiling 180 when the gantry structure 120 is mounted to the ceiling 180.

Figure 4:
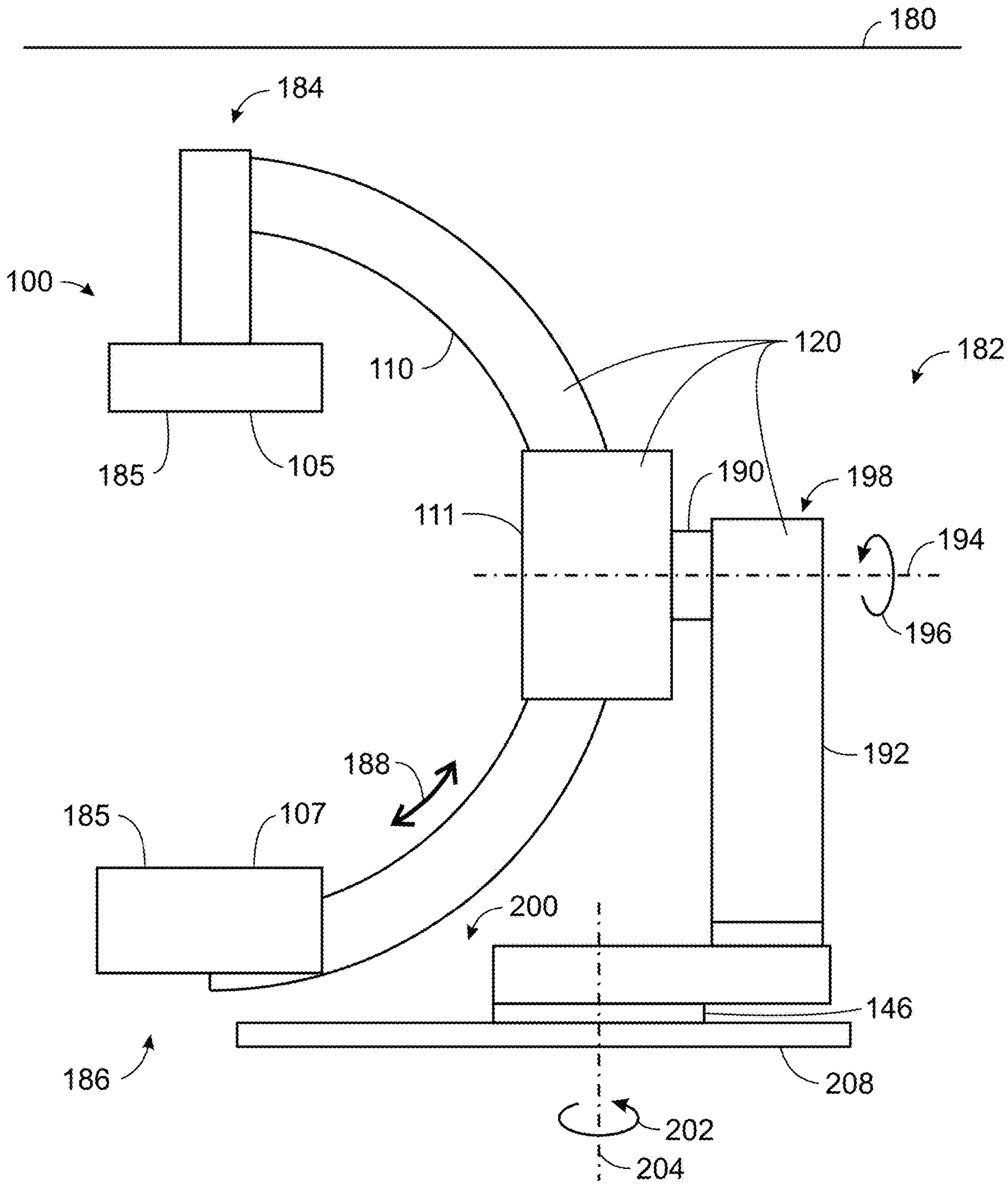
FIG. 4 is a schematic diagram of a side view of an X-ray imaging system (e.g., having an L-arm) mounted to a floor, in accordance with aspects of the present disclosure.

FIG. 4 is a schematic diagram of a side view of the X-ray imaging system 100 (e.g., having an L-arm) mounted to the floor 208 (e.g., in a room 182). The X-ray imaging system 100 includes the C-arm gantry 110. In certain embodiments, the C-arm gantry 110 is made of carbon fiber. The X-ray imaging system 100 also includes the X-ray radiation source 105 coupled to the first end 184 of the C-arm gantry 110 and the X-ray detector 107 coupled to the second end 186 of the C-arm gantry 110 opposite the first end 184 (e.g., forming the image chain 185).

The C-arm gantry 110 is coupled to the C-arm carrier 111 (e.g., C-arm rotation device) that is configured to rotate the C-arm gantry 110 in an orbital direction 188 relative to the C-arm carrier 111 about an isocenter (of the X-ray radiation source 105 and the X-ray detector 107). The C-arm carrier 111 includes rollers (e.g., guiding rollers) to guide movement of the C-arm gantry 110 relative to the C-arm carrier 111.

The C-arm carrier 111 is coupled to the pivot 190 (e.g., pivot point or shaft). The pivot 190 is coupled to a structure 192. The pivot 190 (in conjunction with a motorized system)

is configured to rotate both the C-arm carrier 111 and the C-arm gantry 110 about a rotational axis 194 (e.g., horizontal axis) of the pivot 190 as indicated by arrow 196. In certain embodiments, the structure 192 is an L-arm is coupled via the damping system 146 to the floor 208. The pivot 190 is coupled to a first end 198 of the L-arm and the damping system 146 is coupled to a second end 200 of the L-arm. The damping system 146 is configured to couple the gantry structure 120 to the floor 208 (and, thus, mount the X-ray imaging system 100 to the floor 208). In certain embodiments, the L-arm may rotate about an end of the L-arm coupled to the damping system 146 via the swivel bearing of the damping system 146. In particular, the L-arm (and the gantry structure 120) rotate in direction 202 about a rotational axis 204 of the swivel bearing. The damping system 146 is directly coupled to the floor 208.

The damping system 146 is configured to dampen vibrations caused by motion of the gantry structure 120 for an entirety of the gantry structure 120. For example, the movement of the gantry structure 120 may include the rotational movement of the C-arm gantry 110 in the orbital direction 188, rotational movement in the direction 196 about the axis 194 of the pivot 190 where the C-arm carrier 111 is coupled to an end of the structure 192 (e.g., L-arm), and/or rotational movement in the direction 202 about the 204 axis of where the damping system 146 (e.g., axis 204 of the swivel bearing) is coupled to the floor 208. The damping system 146 is configured to dampen vibrations caused by movement of the gantry structure 120 for an entirety of the gantry structure 120 along the multiple directions. The multiple directions may include orthogonal directions. For example, the orthogonal directions may include a vertical direction extending between a floor 208 and the ceiling 180 and a horizontal direction that is both perpendicular to the vertical direction and parallel with the floor 208 as depicted in FIG. 2.

In certain embodiments, the damping system includes a swivel bearing (e.g., which couples the gantry structure to the floor 208) and a damping mechanism. The damping mechanism includes a body having a first end and a second end opposite the first end, a first damper connection disposed on the first end, and a second damper connection coupled to the second end. In certain embodiments, both the first damper connection and the second damper connection both directly contact both the gantry structure 120 and the body. In certain embodiments, the first damper connection includes one or more damping pads or dampers (e.g., made of elastomeric material such as rubber). In certain embodiments, the second damper connection includes a shaft and bushings coupled to opposite ends of the shaft, and wherein the shaft extends through a portion of the gantry structure 120. In certain embodiments, the swivel bearing is disposed on a surface of the body facing the floor 208 when the gantry structure 120 is mounted to the floor 208.

Figure 5:
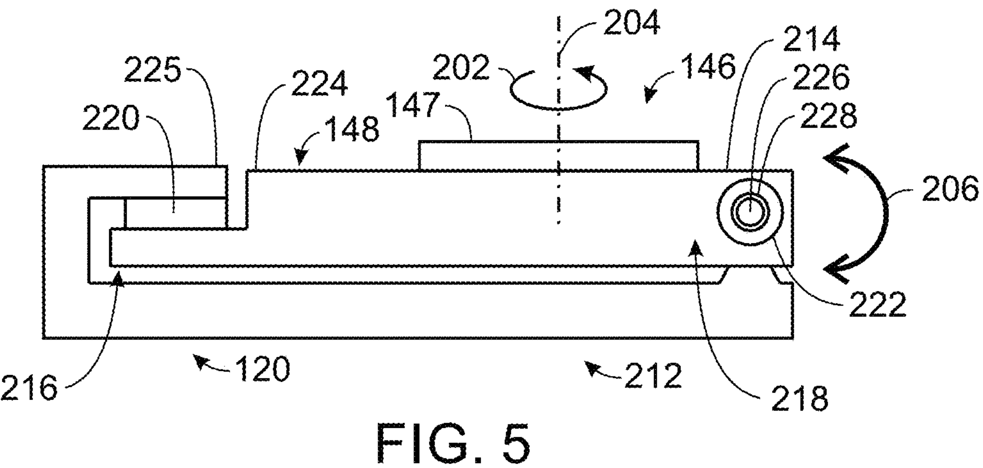
FIG. 5 is a schematic diagram of a lateral view of a damping system configured to mount the X-ray imaging system to a ceiling, in accordance with aspects of the present disclosure.
Figure 6:
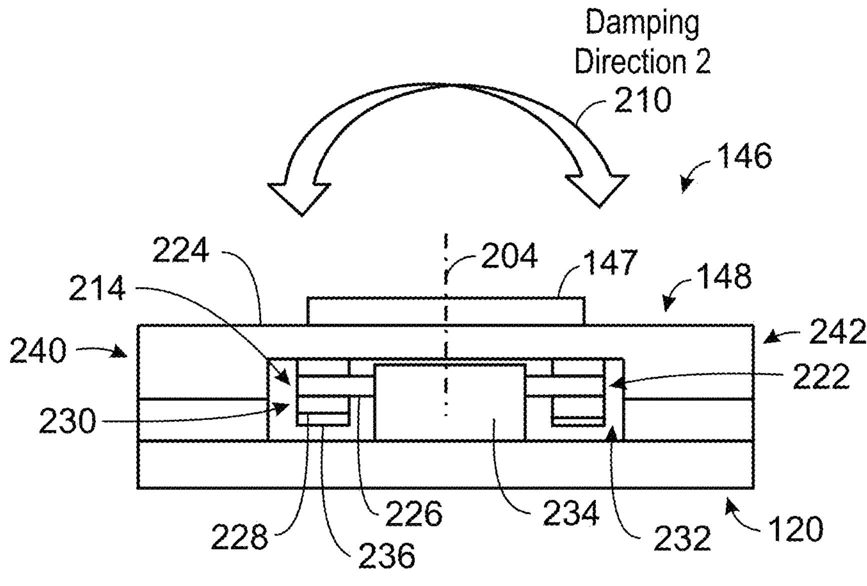
FIG. 6 is a schematic diagram of a cross-sectional front view of the damping system in FIG. 5, in accordance with aspects of the present disclosure.
Figure 7:
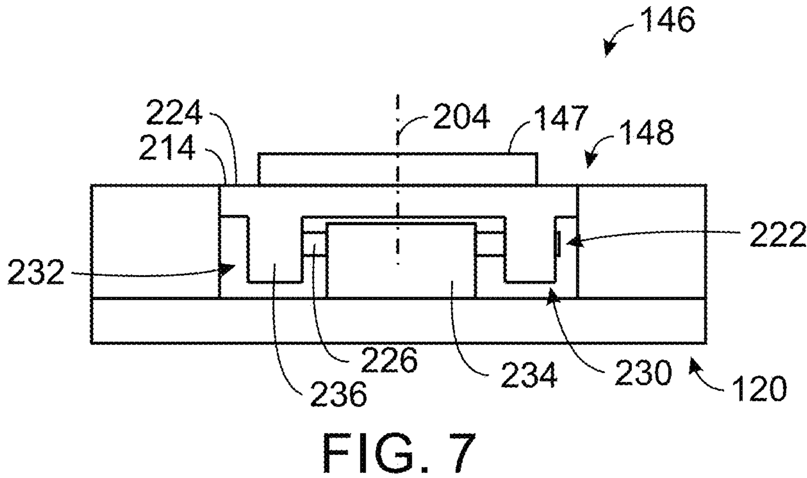
FIG. 7 is a schematic diagram of a back view of the damping system in FIG. 5, in accordance with aspects of the present disclosure.

FIGS. 5-7 are different views of the damping system 146 configured to mount the X-ray imaging system (X-ray imaging system 100 in FIG. 1) to a ceiling. FIG. 5 is a schematic diagram of a lateral view of the damping system 146 configured to mount the X-ray imaging system to a ceiling. FIG. 6 is a schematic diagram of a cross-sectional front view of the damping system 146 in FIG. 5. FIG. 7 is a schematic diagram of a back view of the damping system 146 in FIG. 5.

As depicted in FIGS. 5-7, the damping system 146 is coupled to the gantry structure 120 of the X-ray imaging system. Only a portion 212 of the gantry structure 120 is shown in FIGS. 5-7. In certain embodiments, the portion 212 of the gantry structure 120 may be a L-arm or other structure (e.g., structure 192 in FIG. 2). In certain embodiments, the portion 212 of the gantry structure 120 may be a C-arm carrier (e.g., C-arm carrier 111 in FIG. 3).

The damping system 146 is configured to be suspended from the ceiling. The damping system 146 includes a swivel bearing 147 and a damping mechanism 148. The damping mechanism 148 includes a body 214 having a first end 216 and a second end 218 opposite the first end 216, a first damper connection 220 disposed on the first end 216, and a second damper connection 222 coupled to the second end 218. As depicted, both the first damper connection 220 and the second damper connection 222 both directly contact both the gantry structure 120 and the body 214. In certain embodiments, the first damper connection 220 includes one or more damping pads or dampers (e.g., made of an elastomeric material such as rubber). The first damper connection 220 is disposed on a top surface 224 of the body 214 (e.g., facing the ceiling). In particular, the first damper connection 220 is disposed between and contacts the gantry structure 120 and the body 214. A portion 225 of the gantry structure 120 is located above the first damper connection 220.

As depicted, the second damper connection 222 includes a shaft 226 and bushings 228 coupled to opposite ends 230, 232 of the shaft 226. As depicted, the shaft 226 extends through both a portion 234 of the gantry structure 120 and portions 236 of the body 214 located on a bottom surface 238 (e.g., facing away from the ceiling) of the body 214. In certain embodiments, the body 214 is made of a material that is at least times stiffer than both the first damper connection 220 and the second damper connection 222. The stiffer body 214 minimizes the movement of the gantry structure 120 during damping of vibrations. Also, the stiffness of the body 214 enables the damping system 146 to be safe (i.e., allowing the X-ray imaging system to be stable) even if the damping system 146 or a portion of the damping system 146 ceases to work.

As depicted, the swivel bearing 147 is disposed on the top surface 224 of the body 214 facing the ceiling when the gantry structure 120 is mounted to the ceiling. The swivel bearing 147 is configured to couple the gantry structure 120 to a mobile base (e.g., the chassis 141 of the mobile base 140 when the X-ray imaging system 100 is mounted to the ceiling 180 as depicted in FIG. 2). The swivel bearing 147 is configured to enable the gantry structure 120 to rotate 360 degrees in the direction 202 about the rotational axis 204 of the swivel bearing 147.

The damping system 146 is configured to dampen vibrations caused by motion of the gantry structure 120 for an entirety of the gantry structure 120 along the multiple directions. The multiple directions may include orthogonal directions. For example, the orthogonal directions may include the vertical direction 206 (damping direction 1) extending between the floor and the ceiling and the horizontal direction 210 (damping direction 2) that is both perpendicular to the vertical direction 206 and parallel with the floor as depicted in FIG. 2 and FIGS. 5 and 6. As depicted in FIGS. 5 and 6, the damping directions 1 and 2 may include a circumferential element (e.g., about a rotational axis of the shaft 226 and side to side movement of lateral sides 240, 242 of the damping system 146, respectively).

Figure 8:
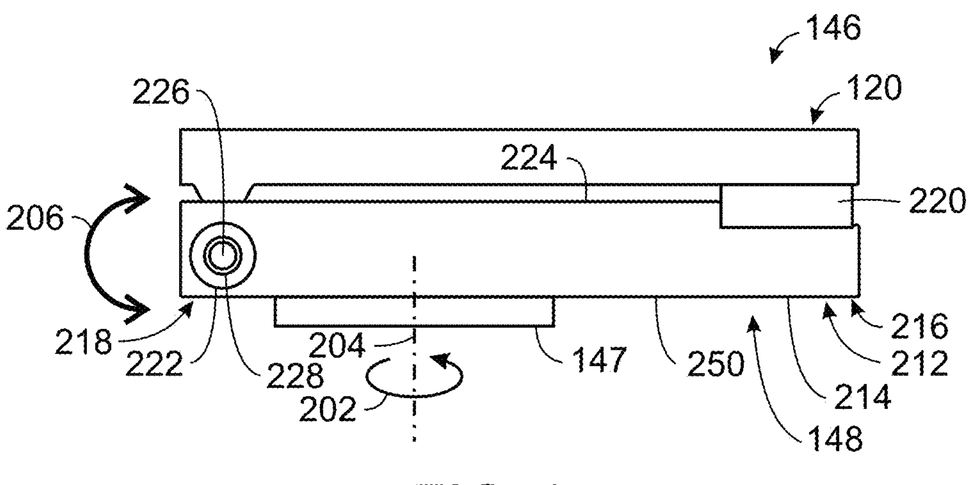
FIG. 8 is a schematic diagram of a lateral view of a damping system configured to mount the X-ray imaging system to a ceiling, in accordance with aspects of the present disclosure.
Figure 9:
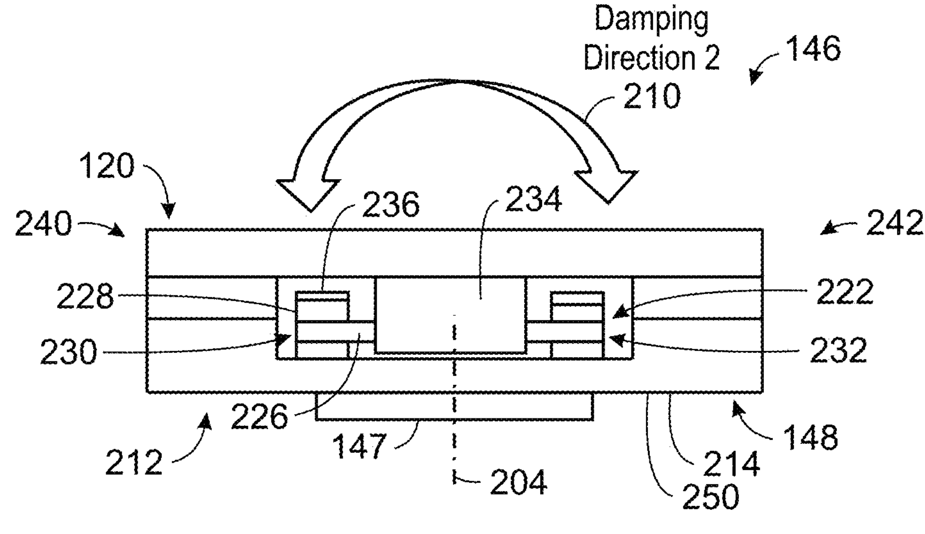
FIG. 9 is a schematic diagram of a cross-sectional front view of the damping system in FIG. 8, in accordance with aspects of the present disclosure.
Figure 10:
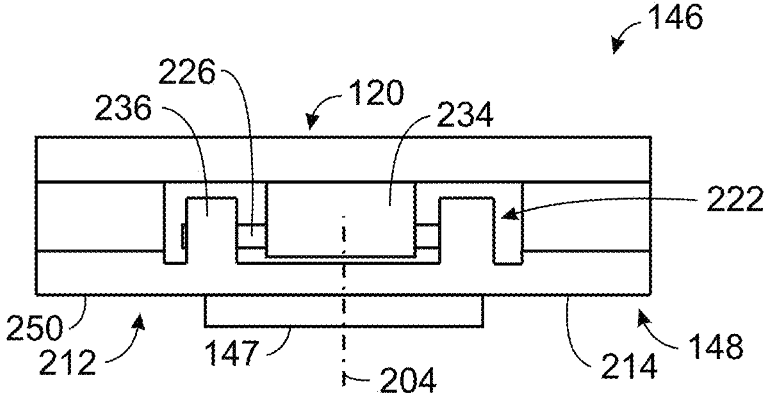
FIG. 10 is a schematic diagram of a back view of the damping system in FIG. 8, in accordance with aspects of the present disclosure.

FIGS. 8-10 are different views of the damping system 146 configured to mount the X-ray imaging system (X-ray imaging system 100 in FIG. 1) to a floor. FIG. 8 is a schematic diagram of a lateral view of the damping system 146 configured to mount the X-ray imaging system to a floor. FIG. 9 is a schematic diagram of a cross-sectional front view of the damping system 146 in FIG. 8. FIG. 10 is a schematic diagram of a back view of the damping system 146 in FIG. 9.

As depicted in FIGS. 8-10, the damping system 146 is coupled to the gantry structure 120 of the X-ray imaging system. Only a portion 212 of the gantry structure 120 is shown in FIGS. 8-10. In certain embodiments, the portion 212 of the gantry structure 120 may be a L-arm or other structure (e.g., structure 192 in FIG. 4).

The damping system 146 includes a swivel bearing 147 and a damping mechanism 148. The damping mechanism 148 includes a body 214 having a first end 216 and a second end 218 opposite the first end 216, a first damper connection 220 disposed on the first end 216, and a second damper connection 222 coupled to the second end 218. As depicted, both the first damper connection 220 and the second damper connection 222 both directly contact both the gantry structure 120 and the body 214. In certain embodiments, the first damper connection 220 includes one or more damping pads or dampers (e.g., made of an elastomeric material such as rubber). The first damper connection 220 is disposed on a top surface 224 of the body 214 (e.g., facing the ceiling). In particular, the first damper connection 220 is disposed between and contacts the gantry structure 120 and the body 214.

As depicted, the second damper connection 222 includes a shaft 226 and bushings 228 coupled to opposite ends 230, 232 of the shaft 226. As depicted, the shaft 226 extends through both a portion 234 of the gantry structure 120 and portions 236 of the body 214 located on the top surface 224 (e.g., facing away from the floor) of the body 214. In certain embodiments, the body 214 is made of a material that is at least times stiffer than both the first damper connection 220 and the second damper connection 222. The stiffer body 214 minimizes the movement of the gantry structure 120 during damping of vibrations. Also, the stiffness of the body 214 enables the damping system 146 to be safe (i.e., allowing the X-ray imaging system to be stable) even if the damping system 146 or a portion of the damping system 146 ceases to work.

As depicted, the swivel bearing 147 is disposed on bottom surface 250 of the body 214 facing the floor when the gantry structure 120 is mounted to the floor. In certain embodiments, the swivel bearing is configured to couple the gantry structure 120 directly to the floor (e.g., wherein there is an absence of a mobile base such as depicted in FIG. 4). In certain embodiments, the swivel bearing 147 is configured to couple the gantry structure 120 to a mobile base (e.g., a chassis of the mobile base when the X-ray imaging system 100 is mounted to the floor). The swivel bearing 147 is configured to enable the gantry structure 120 to rotate 360 degrees in the direction 202 about the rotational axis 204 of the swivel bearing 147.

The damping system 146 is configured to dampen vibrations caused by motion of the gantry structure 120 for an entirety of the gantry structure 120 along the multiple directions. The multiple directions may include orthogonal directions. For example, the orthogonal directions may include the vertical direction 206 (damping direction 1) extending between the floor and the ceiling and the horizontal direction 210 (damping direction 2) that is both perpendicular to the vertical direction 206 and parallel with the floor as depicted in FIG. 2 and FIGS. 8 and 9. As depicted in FIGS. 8 and 9, the damping directions 1 and 2 may include a circumferential element (e.g., about a rotational axis of the shaft 226 and side to side movement of lateral sides 240, 242 of the damping system 146, respectively).

Figure 11:
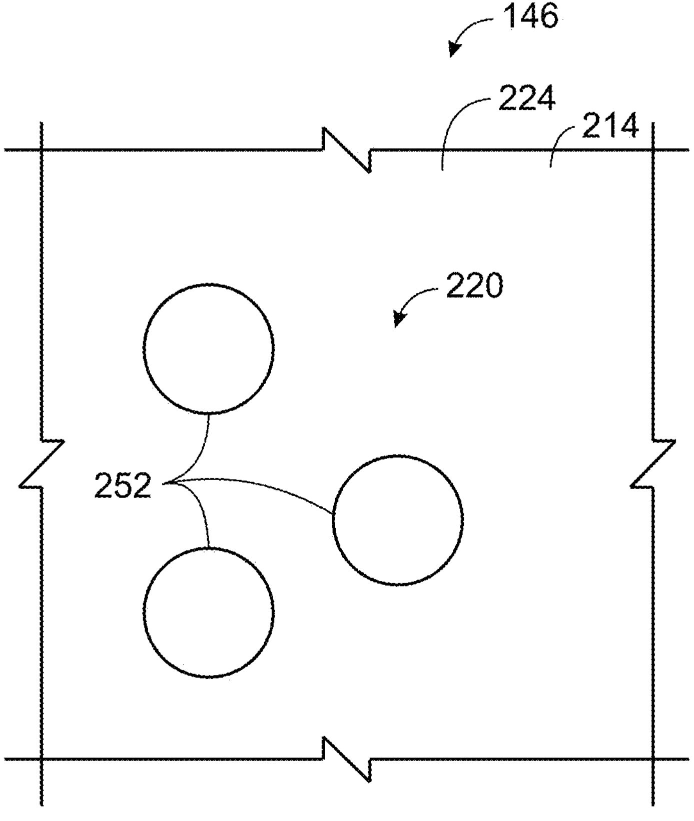
FIG. 11 is a schematic diagram of a portion of a damping system, in accordance with aspects of the present disclosure.

FIG. 11 is a schematic diagram of a portion of the damping system 146. In particular, FIG. 11 is a top view of the top surface 224 of the body 214. As depicted, the first damper connection 220 is disposed on the top surface 224 of the body 214. As depicted, the first damper connection 220 includes a plurality of damping pads or dampers 252 disposed in spaced out arrangement on the top surface 224 of the body 214. In certain embodiments, the number of damping pads 252 may vary (e.g., 1, 2, 3, 4, 5 or more damping pads 252). The shape of the damping pads 252 may vary. The size of the damping pads 252 may also vary. In certain embodiments, a single large damping pad 252 may be disposed on the top surface 224 of the body 214. In certain embodiments, as depicted in FIG. 11, multiple smaller damping pads 252 (i.e., smaller to a large damping pad) are disposed on the top surface 224 of the body 214. The damping pads 252 may be made of an elastomeric material. For example, in certain embodiments, the damping pads 252 may be made of rubber.

Technical effects of the disclosed embodiments include providing a damping system for an X-ray imaging system mounted to a floor or a ceiling in a room. Technical effects of the disclosed embodiments also include dampening motion (e.g., vibrations) caused by floor or ceiling gantry motion in multiple axes or directions. Technical effects of the disclosed embodiments further include enabling the use of a structure (e.g., as part of the gantry structure such as the C-arm) with a low damping coefficient (e.g., relative to aluminum) due to its nature or size. Technical effects of the disclosed embodiments further include enabling the gantry structure (e.g., C-arm) to move with a higher speed (e.g., up to 100 degrees per second speed capacity) to make three-dimensional (3D) reconstruction faster but without causing a regression in image quality. Technical effects of the disclosed embodiments include still further reducing workflow time. Technical effects of the disclosed embodiments also include improving patient comfort. The damping system is also safe (i.e., allowing the X-ray imaging system to be stable) even if the damping system ceases to work.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112 (f). However, for any claims containing elements designated in any other manner, it is intended that such elements are not to be interpreted under 35 U.S.C. 112 (f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An X-ray imaging system, comprising:
an X-ray radiation source;
an X-ray detector;
a gantry structure configured to be mounted to a ceiling or a floor, wherein the gantry structure comprises:
a C-arm having the X-ray radiation source disposed on a first end and the X-ray detector disposed on a second end opposite the first end; and
a C-arm rotation device coupled to the C-arm and configured to rotate the C-arm in an orbital direction relative to the C-arm rotation device; and
a damping system coupled to the gantry structure and disposed between the gantry structure and the ceiling or the floor, wherein the damping system is configured to dampen vibrations caused by motion of the gantry structure for an entirety of the gantry structure, and wherein the damping system comprises a swivel bearing and a damping mechanism.

2. The X-ray imaging system of claim 1, wherein the damping mechanism comprises a body having a third end and a fourth end opposite the third end, a first damper connection disposed on the third end, and a second damper connection coupled to the fourth end.

3. The X-ray imaging system of claim 2, wherein both the first damper connection and the second damper connection both directly contact both the gantry structure and the body.

4. The X-ray imaging system of claim 2, wherein the first damper connection comprises one or more damping pads.

5. The X-ray imaging system of claim 2, wherein the second damper connection comprises a shaft and bushings coupled to opposite ends of the shaft, and wherein the shaft extends through a portion of the gantry structure.

6. The X-ray imaging system of claim 2, wherein the swivel bearing is disposed on a surface of the body facing the floor when the gantry structure is mounted to the floor.

7. The X-ray imaging system of claim 2, wherein the swivel bearing is disposed on a surface of the body facing the ceiling when the gantry structure is mounted to the ceiling.

8. The X-ray imaging system of claim 2, wherein the body is made of a material that is at least times stiffer than both the first damper connection and the second damper connection.

9. The X-ray imaging system of claim 1, wherein the swivel bearing is configured to enable the gantry structure to rotate 360 degrees about a rotational axis of the swivel bearing.

10. The X-ray imaging system of claim 1, wherein the damping system is configured to dampen the vibrations for the entirety of gantry structure along multiple directions.

11. The X-ray imaging system of claim 10, wherein the multiple directions comprise orthogonal directions, and wherein the orthogonal directions comprise a vertical direction extending between the floor and the ceiling and a horizontal direction that is both perpendicular to the vertical direction and parallel with the floor.

12. The X-ray imaging system of claim 1, wherein the C-arm is made of carbon fiber.

13. A damping system for an X-ray imaging system, comprising:
a damping mechanism, comprising:
a body configured to couple to a gantry structure of the X-ray imaging system, wherein the X-ray imaging system comprises the gantry structure, an X-ray radiation source, and an X-ray detector, and the gantry structure is configured to be mounted to a ceiling or a floor, and the gantry structure comprises a C-arm having the X-ray radiation source disposed on a first end and the X-ray detector disposed on a second end opposite the first end, and a C-arm rotation device coupled to the C-arm and configured to rotate the C-arm in an orbital direction relative to the C-arm rotation device, and wherein the body has a third end and a fourth end opposite the third end;
a first damper connection disposed on the third end; and
a second damper connection coupled to the fourth end; and
swivel bearing configured to enable the gantry structure to rotate 360 degrees about a rotational axis of the swivel bearing, wherein the damping system is configured to dampen vibrations caused by motion of the gantry structure for an entirety of the gantry structure.

14. The damping system of claim 13, wherein both the first damper connection and the second damper connection both directly contact both the gantry structure and the body, wherein the first damper connection comprises one or more damping pads, and the second damper connection comprises a shaft and bushings coupled to opposite ends of the shaft, and wherein the shaft extends through a portion of the gantry structure.

15. The damping system of claim 13, wherein the swivel bearing is disposed on a surface of the body facing the floor when the gantry structure is mounted to the floor.

16. The damping system of claim 13, wherein the swivel bearing is disposed on a surface of the body facing the ceiling when the gantry structure is mounted to the ceiling.

17. The damping system of claim 13, wherein the body is made of a material that is at least times stiffer than both the first damper connection and the second damper connection.

18. The damping system of claim 13, wherein the damping system is configured to dampen the vibrations for the entirety of the gantry structure along orthogonal directions, and wherein the orthogonal directions comprise a vertical direction extending between the floor and the ceiling and a horizontal direction that is both perpendicular to the vertical direction and parallel with the floor.

19. An X-ray imaging system, comprising:
an X-ray radiation source;
an X-ray detector;
a gantry structure configured to be mounted to a ceiling, wherein the gantry structure comprises:
a C-arm having the X-ray radiation source disposed on a first end and the X-ray detector disposed on a second end opposite the first end, wherein the C-arm is made of carbon fiber; and
a C-arm rotation device coupled to the C-arm and configured to rotate the C-arm in an orbital direction relative to the C-arm rotation device; and
a damping system coupled to the gantry structure and disposed between the gantry structure and the ceiling, wherein the damping system is configured to dampen vibrations caused by motion of the gantry structure for an entirety of the gantry structure along orthogonal directions, and wherein the orthogonal directions comprise a vertical direction extending between a floor and the ceiling and a horizontal direction that is both perpendicular to the vertical direction and parallel with the floor.

* * * * *